United States Patent [19]

Fujii et al.

[11] Patent Number: 4,659,617

[45] Date of Patent: Apr. 21, 1987

[54] FIBROUS APATITE AND METHOD FOR PRODUCING THE SAME

[75] Inventors: Shigeo Fujii, Kawagoe; Shoichi Mori; Jyoichi Tabuchi, both of Oi, all of Japan

[73] Assignee: Toa Nenryo Kogyo Kabushiki Kaisha, Tokyo, Japan

[21] Appl. No.: 773,482

[22] Filed: Sep. 6, 1985

[30] Foreign Application Priority Data

| | | |
|---|---|---|
| Sep. 11, 1984 [JP] | Japan | 59-190413 |
| Sep. 14, 1984 [JP] | Japan | 59-193159 |
| Oct. 31, 1984 [JP] | Japan | 59-229283 |
| Oct. 31, 1984 [JP] | Japan | 59-229284 |
| Feb. 26, 1985 [JP] | Japan | 60-35262 |
| Feb. 26, 1985 [JP] | Japan | 60-35263 |

[51] Int. Cl.$^4$ .......... B32B 7/02; C01B 15/16; A61C 8/00; B29C 33/40
[52] U.S. Cl. .......... 428/221; 501/1; 423/305; 433/201.1; 264/220
[58] Field of Search .......... 428/221; 501/1, 151; 423/305, 308, 309; 433/201.1; 264/220, 221, 225

[56] References Cited

U.S. PATENT DOCUMENTS

| | | | |
|---|---|---|---|
| 4,113,500 | 9/1978 | Ebihara et al. | 501/1 |
| 4,146,936 | 4/1979 | Aoyagi et al. | 3/1.91 |
| 4,371,484 | 2/1983 | Inukai et al. | 264/44 |
| 4,481,175 | 11/1984 | Iino et al. | 423/308 |
| 4,497,075 | 2/1985 | Niwa et al. | 3/1.9 |
| 4,503,157 | 3/1985 | Hatahira | 501/1 |

FOREIGN PATENT DOCUMENTS

| | | | |
|---|---|---|---|
| 0110465 | 7/1983 | Japan | 501/151 |
| 1487181 | 9/1977 | United Kingdom | 501/1 |

*Primary Examiner*—John E. Kittle
*Assistant Examiner*—Patrick J. Ryan
*Attorney, Agent, or Firm*—Seidel, Gonda, Goldhammer & Abbott

[57] ABSTRACT

The present invention provides a fibrous product of apatite comprising one or more apatites selected from a group of apatites represented by the general formula:

$$M_{10}(ZO_4)_6X_2$$

wherein M represents Ca, Ba, Mg, Sr, Pb, Cd, Fe and the like, $ZO_4$ represents $PO_4$, $AsO_4$, $VO_4$, $CO_3$ and the like, and X represents F, Cl, OH and the like. This fibrous product of apatite has many applications such as uses for medical treatment, large scale microorganism cultivating media and others, and particularly it is useful as apatite implant materials having a good compatibility with living organism and superior workability.

A fibrous apatite product of this invention may be produced by a method comprising the steps of:
(a) preparing a dispersion of apatite by dispersing fine apatite particles uniformly in a solution of binder in water, said apatite being one or more apatites selected from a group of apatites represented by the general formula:

$$M_{10}(ZO_4)_6X_2$$

wherein M represents Ca, Ba, Mg, Sr, Pb, Cd, Fe and the like, $ZO_4$ represents $PO_4$, $AsO_4$, $VO_4$, $CO_3$ and the like, and X represents F, Cl, OH and the like;
(b) continuously exctruding the thus prepared dispersion through a plurality of spinning orifices in a spinning apparatus while simultaneously stretching the dispersion into a fibrous state with the aid of a high speed air flow to form a stream of fine fibers;
(c) heating said fiber stream to evaporate the water in the fibers;
(d) blowing said dewatered fiber stream upon a collector means to form a cotton-like product of apatite bonded together by the binder; and
(e) if desired, calcining said cotton-like product.

24 Claims, 6 Drawing Figures

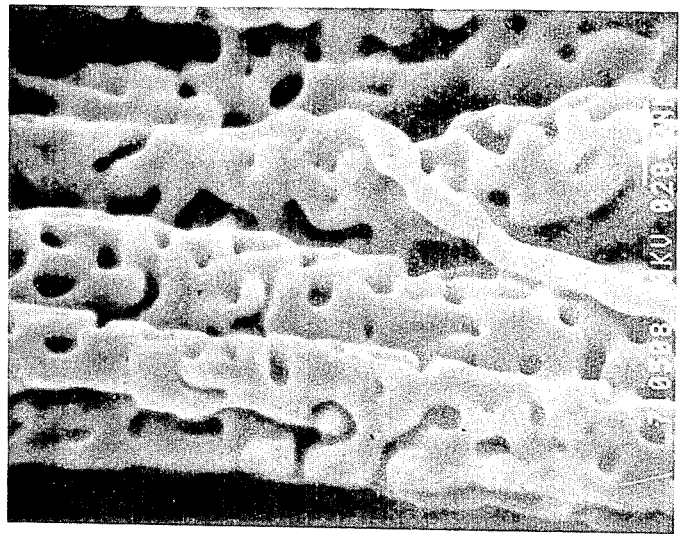
FIG.5B AFTER CALCINING
MAGNIFICATION × 4000
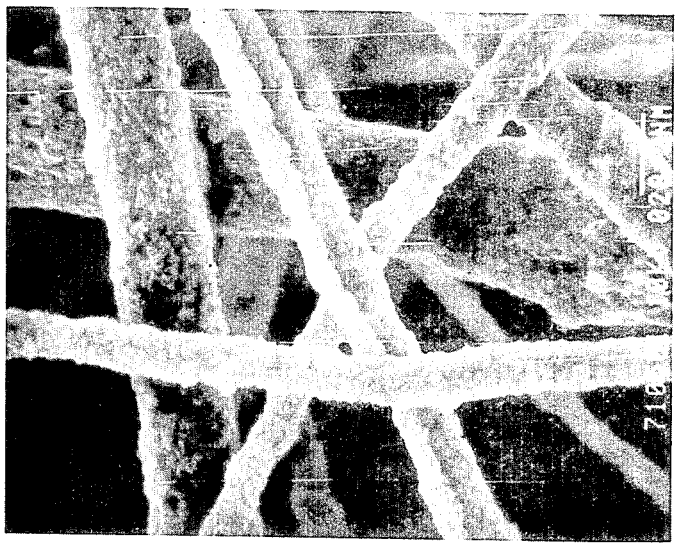
FIG.5A PRIOR TO CALCINING
MAGNIFICATION × 4000

FIBROUS APATITE AND METHOD FOR PRODUCING THE SAME

TECHNICAL FIELD

This invention relates to an apatite material in fibrous form and a method for producing the same, and particularly to apatite materials in fibrous form, particularly in cotton-like and nonwoven fabric form having many applications such as uses for medical treatment, large scale microorganism cultivating media or others, and a method for manufacturing such materials. More particularly, this invention relates to apatite implant materials having good compatibility with living organism and a high working efficiency, and a method for fabricating the same.

BACKGROUND ART

Artificial implant materials conventionally used for remedying breaks or voids made in bones or tooth roots by excision include the patient's own bones, similar bones provided by close relatives, other dissimilar bones, and metallic, organic and carbon materials. However, if a patient's own bone is to be used, the patient would suffer a severe pain in that a bone organization must be cut from a location other than the affected part. In addition, there may not always be sufficient bone available to provide an adequate amount of bone required for the remedy, so that it is often required to use a substitute to make up the shortage. In order to utilize similar or dissimilar bones other than a patient's own as a substitute, it is required to perform a surgical operation on an other living organism, which would impose a heavy burden on the bone donor.

On the other hand, metallic implant materials do not only lack affinity with living organism, but also have the disadvantage that metallic ions will plate out of the implant material into the human body, resulting in deterioration of the material. Such metallic ions may also be poisonous to man. For these reasons, metallic implant materials have proven unsuitable for permanent use. This is also true of organic and carbon materials.

In an attempt to overcome the aforesaid disadvantages, single-crystal or polycrystal alumina, silica, alumina or calcium phosphate-based glass, and ceramics such as apatite (see Japanese Patent Application Public Disclosure No. 52-64199, for example) have recently been proposed for use as implant materials. Composite materials comprising a metallic core flame spray coated with hydroxy-apatite powders are also known as disclosed in Japanese Patent Application Public Disclosure No. 52-82893. These ceramic materials are superior to other materials in that they have a high affinity with living organism and provide direct and intimate connection with bone organization. Especially, hydroxy-apatite is known to be a main inorganic ingredient of a bone or tooth. In this regard, calcined synthetic hydroxy-apatite draws an increasing attention as so-called artificial implant materials for artificial tooth, bone and the like since such apatite exhibits so good affinity with bone and tooth organizations as to bond directly and chemically with the bone organization and gums. (See, for example, The Chemistry and Industry, Vol. 37, No. 4, P.243, 1984.) Artificial tooth roots of calcined apatite and artificial bones of porous apatite have reached the stage of practical use.

However, calcined apatite is a brittle material which is vulnerable to tension, although highly resistant to compression, so that such apatite tends to have its tensile strength greatly reduced if a hair crack should be developed on the surface of the apatite due to a shock. This narrows down the width of application of calcined apatite to living organism. The use of such material has thus been limited only to artificial tooth roots for molar teeth or the like where no excessive tensile stress will be exerted. Moreover, when such material is to be used as fillers for breaks in bone, difficulties are involved in shaping the material in conformity with the intricate contour of the affected part.

In an attempt to eliminate the shortcomings of the calcined apatite described above, Japanese Patent Application Public Disclosures Nos. 57-117621 and 58-54023 disclose inorganic apatite fiber in which the apatite is made fibrous so as to suit the use as implant material for breaks or voids in bone. However, the apatite fiber as disclosed in these patent application public disclosures is fabricated by the so-called melt spinning process involving the steps of melting apatite at a high temperature and spinning it. As stated also in said disclosures, such melt spinning process requires that apatite be melted at a high temperature of 1500° C. As a result, the apatite is deprived of its hydroxy group, and hence the 'affinity'. The apatite fiber thus has a serious disadvantage in that it does not provide adequate compatibility with living organism in contrast to hydroxy-apatite. For this reason, such melt spun apatite fiber required a post-treatment for providing it with 'affinity'.

If apatite is to be made fibrous without being deprived of the hydroxy group, the melt spinning process cannot be employed, but an other method such as the solution spinning process should be taken into consideration. However, since no binder or no spinning or calcining method suitable for use with the solution spinning process has been developed, it has heretofore been impossible to make apatite in fibrous form, particularly in cotton-like or fabric form with the hydroxy group retained as such.

After extensive researches and studies with a view to overcoming the prior art shortcomings as described above, the inventors of the present invention have discovered that it is possible to manufacture fibrous apatite, particularly cotton-like apatite and nonnwoven fabric thereof by solution spinning apatite with the use of special binder to make the apatite in fibrous form, particularly in cotton-like and nonwoven fabric form, and calcining the thus made apatite.

It is accordingly an object of this invention to provide apatite material in fibrous form, particularly in cotton-like and nonwoven fabric form having many applications such as uses for medical treatment, large scale microorganism cultivating media and others.

Another object of this invention is to provide hydroxy-apatite material in fibrous form, particularly in cotton-like and nonwoven fabric form which has excellent compatibility with living organism and superior physical properties such as tensile strength and the like.

Still another object of this invention is to provide a method of producing the apatite material of the type described in fibrous form, particularly in cotton-like and nonwoven fabric form.

Yet another object of this invention is to provide apatite implant material having a good compatibility with living organism and a high workability.

SUMMARY OF THE INVENTION

Briefly, the present invention provides a fibrous product of apatite comprising one or more apatites selected from a group of apatites represented by the general formula:

$$M_{10}(ZO_4)_6X_2$$

wherein M represents Ca, Ba, Mg, Sr, Pb, Cd, Fe and the like, ZO4 represents PO4, AsO4, VO4, CO3 and the like, and X represents F, Cl, OH and the like, and more particularly a fibrous product of apatite in which the apatite is substantially hydroxy-apatite.

This invention may also provide a fibrous product of apatite having calcium phosphate type compound incorporated therein for reinforcement.

A fibrous product of apatite according to this invention may be manufactured in the form of cotton-like product or nonwoven fabric, if desired.

In another aspect, the present invention provides a method of producing a fibrous product of apatite of the type described, comprising the steps of preparing a dispersion of fine apatite particles with the use of a water-soluble high molecular compound, and spinning this dispersion by solution spinning process.

BRIEF DESCRIPTION OF THE DRAWINGS

These and other objects and features of the present invention will be fully understood from the following detailed description of the invention taken with reference to the accompanying drawings, in which:

FIG. 5 is electron micrographs of a cotton-like product of apatite according to this invention prior to and after being calcined, respectively.

DETAILED DESCRIPTION OF THE PREFERRED EMBODIMENTS

Figure 1:
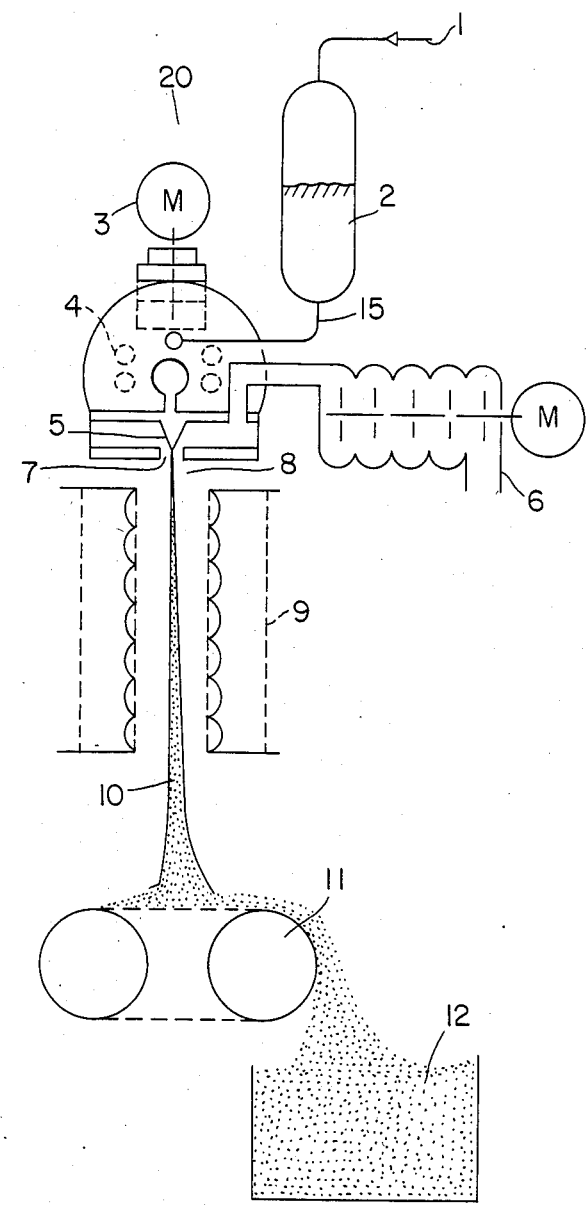
FIG. 1 is a schematic side elevational view of one form of apparatus used for producing a cotton-like product of apatite according to this invention.
Figure 1:
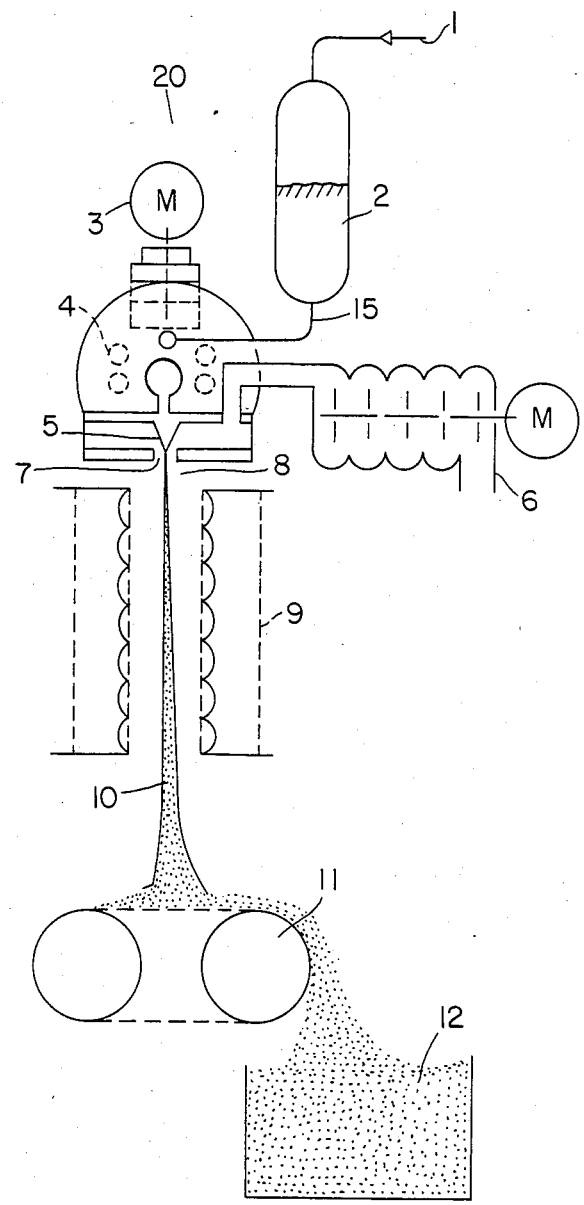

According to this invention, a fibrous product of apatite, particularly in cotton-like form or nonwoven fabric form is provided which comprises one or more apatites selected from a group of apatites represented by the general formula:

$$M_{10}(ZO_4)_6X_2$$

wherein M represents Ca, Ba, Mg, Sr, Pb, Cd, Fe and the like, ZO4 represents PO4, AsO4, VO4, CO3 and the like, and X represents F, Cl, OH and the like.

The term "cotton-like product" herein used is intended to mean what is formed by intertwined fibers as if they were cotton. If desired, a cotton-like product of apatite may be made in the form of nonwoven fabric.

According to this invention, any one or more of apatites as represented by the aforesaid general formula may be selected and employed alone or in combination to obtain a fibrous product of the apatite or apatites used. When producing medical implant materials, calcium phosphate type apatite is preferably used because of its similarity to bone organization. More preferably, hydroxy-apatite (compound as represented by the aforesaid general formula where M is Ca, ZO4 is PO4 and X is OH) is employed from a view point of compatibility with living organism. However, it should be understood that this invention does not preclude the use of such compounds as having members other than Ca, PO4 and OH in the locations of M, ZO4 and X, respectively represented by the aforesaid formula, so long as such other members would not impair the compability with living organism. In other words, two or more kinds of apatite may be employed.

According to a particularly preferred embodiment of this invention, a fibrous product of apatite wherein the apatite is substantially hydroxy-apatite is provided.

Such fibrous product of apatite substantially all of which comprises hydroxy-apatite, however, may not be satisfactory with respect to its strength. In this regard, the fibrous product of apatite may contain inorganic compound such as calcium phosphate type compound, for example therein to enhance the physical properties such as strength and the like. Accordingly, in another preferred embodiment of the invention, a fibrous product of apatite containing a calcium phosphate type compound in addition to hydroxy-apatite is provided. Such compound may be at least one selected from a group of calcium hydrogen phosphate ($CaHPO_4$), tri-calcium phosphate ($Ca_3(PO_4)_2$), and tetra-calcium phosphate ($Ca_4O(PO_4)_2$). These compounds may be contained in the apatite product in an amount of generally 5 to 95 weight %, preferably 80 weight % or less, more preferably 50 weight % or less. Calcium phosphate type compound may be incorporated by initially blending an amount of the compound required into the main ingredient(s), or alternatively by subjecting the hydroxy-apatite to a high temperature treatment to produce such compound from a part of the hydroxy-apatite, as will be described hereinafter.

In a fibrous product of apatite according to this invention the fibers may have generally a mean diameter of 1 μm to 30 μm and a mean length of 1 mm to 1,000 mm. Of course, this is not limitative but just illustrative. As stated before, a fibrous product of apatite according to this invention may be made particularly in cotton-like form or nonwoven fabric. For such nonwoven fabric the basis weight may generally be in the range of 5 g/m² to 500 g/m², but this is not limitative.

A fibrous apatite in cotton-like form of this invention may be produced by a method comprising the steps of:

(a) preparing a dispersion of apatite by dispersing fine apatite particles uniformly in a solution of binder in water, said apatite being one or more apatites selected from a group of apatites represented by the general formula:

$$M_{10}(ZO_4)_6X_2$$

wherein M represents Ca, Ba, Mg, Sr, Pb, Cd, Fe and the like, ZO4 represents PO4, AsO4, VO4, CO3 and the like, and X represents F, Cl, OH and the like;

(b) continuously extruding the thus prepared dispersion through a plurality of spinning orifices in a spinning apparatus while simultaneously stretching the dispersion into a fibrous state with the aid of a high speed air flow to form a stream of fine fibers;

(c) heating said fiber stream to evaporate the water off from the fibers;

(d) blowing said water-removed fiber stream upon a collector means to form a cotton-like product of apatite bonded by the binder; and (e) if desired, calcining said cotton-like product.

According to a preferred embodiment of this invention, a hydroxy-apatite represented by the general formula wherein M is Ca, $ZO_4$ is $PO_4$, and X is OH is employed.

Apatite for the purpose of this invention may be either any suitable one synthesized in a known manner or any natural one. The apatite may be fine particles having a mean particle diameter of 50 Å to 1 μm, and preferably 70 to 500 Å. In this case, while the configuration of apatite particles is not limited to any particular one, it is preferable to use apatite particles in the form of stick since such stick particles facilitate the formation of the apatite into fibrous form or cotton-like form. Although the reason for this has not completely been elucidated, it is presumed that it may be easy to orient the stick-like particles in a predetermined direction during the spinning step. Stick-like particles of apatite such as hydroxy-apatite may be prepared by dropping an aqueous solution of phosphoric acid gradually into an alkaline solution (pH: 7 to 11) containing calcium ions, for example.

Binders used to produce a fibrous product of apatite according to this invention may be commonly known water-soluble binders. Such binders may be water-soluble, cotton-like high molecular compounds having —OH, —COOH, —CONH$_2$ groups or the like in their molecules, including pullulan which is a linear glucan wherein maltotrioses are bonded by recurring α-1, 6-glycoside linkages, polyvinyl alcohol, polyacrylamide, polyacrylic acid, polymethacrylic acid, polyitaconic acid, polyethylene oxide, polyvinyl pyrolidone, polyvinyl methylene ether, hydroxypropyl cellulose, xanthane gum, guar gum, collagen, hydroxyethyl cellulose, carborymethylcellulose and the like. While there is no particular limitation as to the molecular weight, such high molecular compounds may have a molecular weight of preferably 20,000 to 2,000,000, and more preferably 50,000 to 1,000,000.

When fibrous products of apatite according to this invention are to be used particularly as medical materials, it is desirable that binders should meet at least two conditions that they be harmless to living organism and water-soluble. Suitable examples of such binders may include high molecular compounds such as polyvinyl alcohol, carboxymethylcellulose, hydroxypropylcellulose, collagen and the like and high molecular polysaccharides such as pullulan, chitin, dextran and the like. Pullulan is particularly suitable.

According to this invention, a dispersion comprising apatite particles dispersed in an aqueous solution of the binder as described above is subjected to a spinning step. Thus, the composition of the feed dispersion should be in a predetermined range. By way of example, for hydroxy-apatite, its composition may comprise 10 to 90 weight %, preferably 50 to 70 weight %, more preferably 60 to 65% of water, 5 to 70 weight %, preferably 15 to 30 weight %, more preferably 15 to 20 weight % of hydroxy-apatite, and 5 to 40 weight %, preferably 15 to 30 weight %, more preferably 20 to 25 weight % of binder. If the amount of hydroxy-apatite is less than 5 weight %, it would not be able to provide a fibrous apatite material having sufficient strength. Conversely, more than 70 weight % of hydroxy-apatite would undesirably increase the viscosity excessively.

For the purpose of improving the dispersion of hydroxy-apatite in feedstock liquid, organic carboxylic acid, or plasticizers or softening agents including polyhydric alcohol such as glycerin, sorbitol, maltitol, ethylene glycol, propylene glycol or the like may be added.

Further, inorganic compounds other than apatite, such as calcium phosphate, for example may be added in an amount of less than 5% as a dispersing medium to improve the physical properties of fibrous apatite material obtained.

In the present invention it is preferable to prepare the feedstock solution described above at a temperature of about 20° to 70° C. The thus prepared dispersion is continuously extruded through spinning orifices while simultaneously discharging a gas through gas discharge orifice means adjacent to the spinning orifices at a high speed to form the dispersion into a stream of fibers. The fiber stream is rid of water and collected as a fibrous product in cotton-like form, and then, if desired, the product may be calcined.

In case of hydroxy-apatite, it has been experimentally found by X-ray diffraction and infrared spectrophotometry that the fibrous apatite material, if not calcined or if calcined at a temperature lower than 1250° C., will have the structure of $Ca_{10}(PO_4)_6OH_2$ or $Ca_5(PO_4)_3OH$, whereas if calcined at higher than 1250° C., it will be transformed into the structure of $\alpha$-$Ca_3(PO_4)_2$. Such transformed product does not retain the hydroxy group, resuluting in reduced compatibility with living organism. In order to retain substantially the structure of hydroxy-apatite, it is preferable to carry out the calcining step at a temperature lower than 1250° C., preferably lower than 1200° C.

One embodiment of the method of producing a fibrous product of apatite according to this invention wherein fine hydroxy-apatite particles are used as a raw material will now be described with reference to FIG. 1.

First, hydroxy-apatite, binder and water, and if required, dispersant, plasticizer and/or softener are introduced through a feed line 1 into a feedstock tank 2 to prepare a viscous spinning solution. Such feed spinning solution may be prepared preferably at about 20° to 70° C. This viscous spinning solution is fed through a conduit 15 and then extruded through a spinning nozzle means 5 by a gear pump 4 driven by a motor 3, while simultaneously gas is discharged through an air nozzle means 7 positioned around the spinning nozzle means at a high velocity by a multi-stage blower 6. The spinning nozzle may include a plurality of dies arranged in a straight line in a widthwise direction. A stream 8 of fine fibers stretched and cut in length is formed by discharging gas such as air at about 20° to 60° C. from around the spinning nozzle means at a velocity of about 5 to 1000 m/sec. The diameter and length of the fibers may be adjusted so as to be in the ranges of about 1 to 30 μm and 2 to 1,000 mm, respectively by varying the pressure of gas discharged.

Then, the thus formed stream 8 of fine fibers is heated by a heater such as an infrared heater 9 or the like underlying the spinning nozzle means to evaporate the water off from the fibers to a moisture content of less than 10 weight %, preferably less than about 7 weight % to thereby solidify the fiber stream. It should be noted that excessive removal of water would result in failure to produce a fibrous apatite in cotton-like form composed of fine fibers. In this regard, the temperature of the heater may be generally in the range of about 200° to 500° C. for the fiber stream at about 80° to 150° C. The heating temperature for the fiber stream is selected depending upon the extrusion rate of the spinning solution, and the temperature and volume of the gas blown. Excessively high heating temperature is not desirable in that it would cause decomposition of the binder during the heating step.

The fine fiber stream 10 as stretched, cut in length and water-removed is then blown onto a suitable collector means 11 in the form of a screen type collector vessel or a screen-type collecting belt to be collected and deposited thereon.

Figure 2:
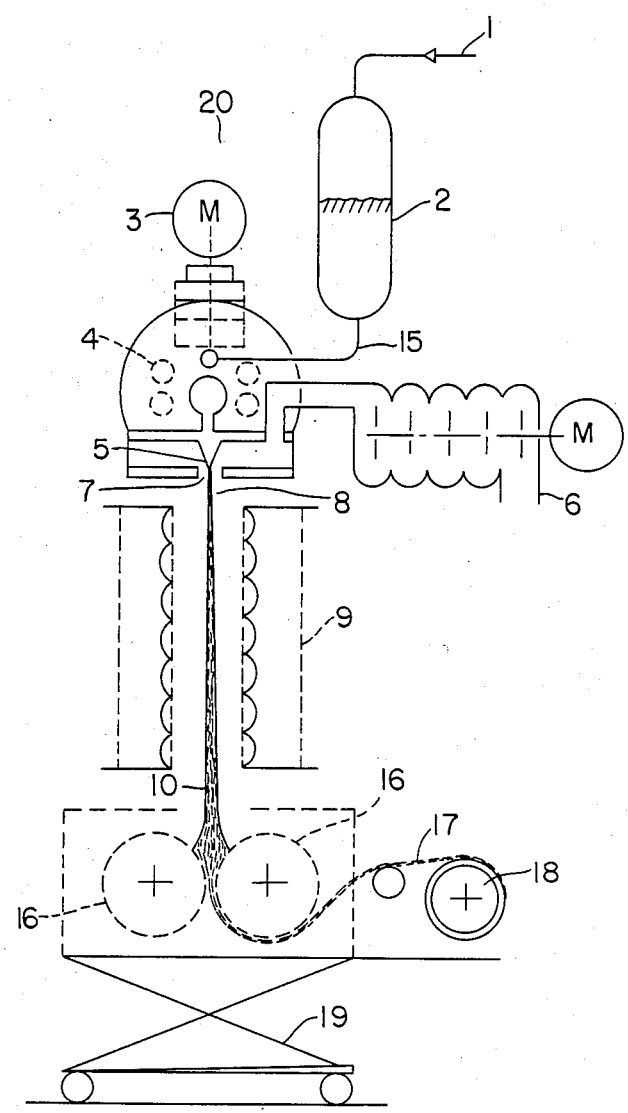
FIG. 2 is a schematic side elevational view of one form of apparatus used for manufacturing nonwoven fabric of apatite according to this invention.

If a fibrous apatite in nonwoven fabric is to be manufactured, the fine fiber stream as stretched and water-removed as described above is caused to drop onto a moving collector means in the form of a screen type rotary drum assembly 16 as shown in FIG. 2 or a moving belt conveyor with the fibers intertwined to form an nonwoven fabric. If the stream of fibers is blown down into the nip between the two rotating screen type drums 16, a bulky nonwoven fabric 17 having the intertwined fibers oriented in a direction of thickness of the nonwoven fabric (that is, in a three-dimensional configuration) will be obtained. In an alternate embodiment, if the fiber stream is blown down onto those areas of the rotating drums other than the nip between the drums or onto a planar collecting belt conveyor, an nonwoven fabric will be produced in which the fibers are oriented parallel in a plane (that is, in a two-dimensional manner). The basis weight of the nonwoven fabric may be regulated so as to be in the range of 5 g/m² to 500 g/m², for example by varying the speed at which the collector means moves.

The thus produced fibrous apatite, namely, cotton-like product or nonwoven fabric of apatite fibers bonded together by the binder provides a feeling soft and agreeable to the touch. Further, owing to its hydrophilic nature, moisture-absorption characteristics and non-electrifying property as well as its cultivation promoting effect, such cotton-like product or nonwoven fabric of apatite in an uncalcined state may be employed as a culture medium for microorganisms.

Uncalcined cotton-like product or nonwoven fabric may be calcined at a temperature of about 500° to 1250° C., preferably about 600° to 1200° C., more preferably 650° to 1100° C. to burn the binder off whereby a fibrous apatite material of this invention is obtained. At the calcining temperature lower than 1200° C. there is very little loss of the hydroxy group, so that no account may be taken of the loss of hydroxy group although it depends somewhat upon the calcining temperature. If required, the calcining temperature higher than 1200° C. may be used to produce $Ca_3(PO_4)_2$ in the hydroxy-apatite to thereby enhance the physical properties such as strength of the cotton-like product or nonwoven fabric of hydroxy-apatite when it is used as implant material.

The thus obtained cotton-like product or nonwoven fabric may be subjected to a further process according to the purpose for which it is to be used. By way of example, collagen may be applied to or impregnated into such product or fabric to further improve the desired properties thereof. It may also be combined with a cultivating substance such as pullulan to suit the use as a large scale culture medium.

A fibrous apatatite material according to another preferred embodiment of this invention containing calcium phosphate-type compound in addition to hydroxy-apatite may be produced by a method comprising the steps of: adding a water-soluble binder to an aqueous solution containing fine particles of hydroxy-apatite and calcium phosphate-type compound to form a viscous dispersion, continuously spinning the dispersion through a plurality of spinning orifices of a spinning machine while simultaneously discharging a gas through gas discharge orifice means adjacent to the spinning orifices at a high velocity to stretch the fibers from the spinning orifices into a stream of fine fibers, heating the fiber stream to remove the water therefrom, and blowing said water-removed fiber stream onto a collector means as in the form of a collecting plate to form a cotton-like product of apatite.

In this case, the composition of the starting dispersion may preferably comprise 5 to 90 weight % of water, 5 to 70 Weight % of apatite, 5 to 70 weight % of calcium phosphate and 2 to 30 weight %. More suitable composition is 25% of water, 35% of hydroxy-apatite, 30% of calcium phosphate, and 10% of pullulan on the basis of weight. The other manufacturing conditions may be the same as for the production of the fibrous product as described hereinbefore substantially all of which comprises apatite.

Examples of the present invention will be described hereinbelow, it being understood that this is not to limit the invention.

EXAMPLE 1

Figure 3:
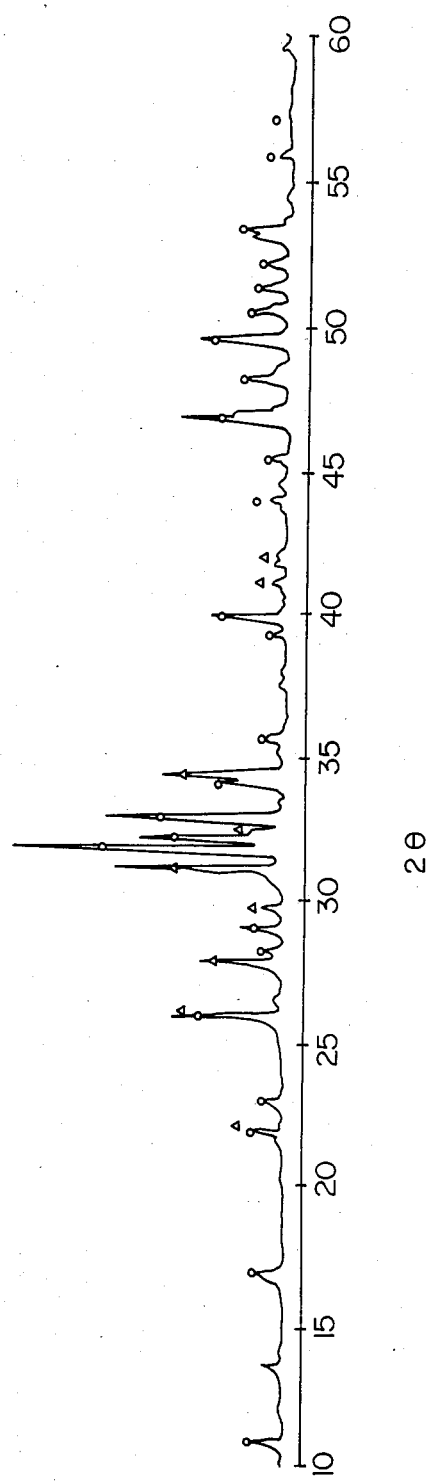
FIG. 3 is an X-ray diffraction pattern of a cotton-like product of hydroxy-apatite according to this invention.
Figure 4:
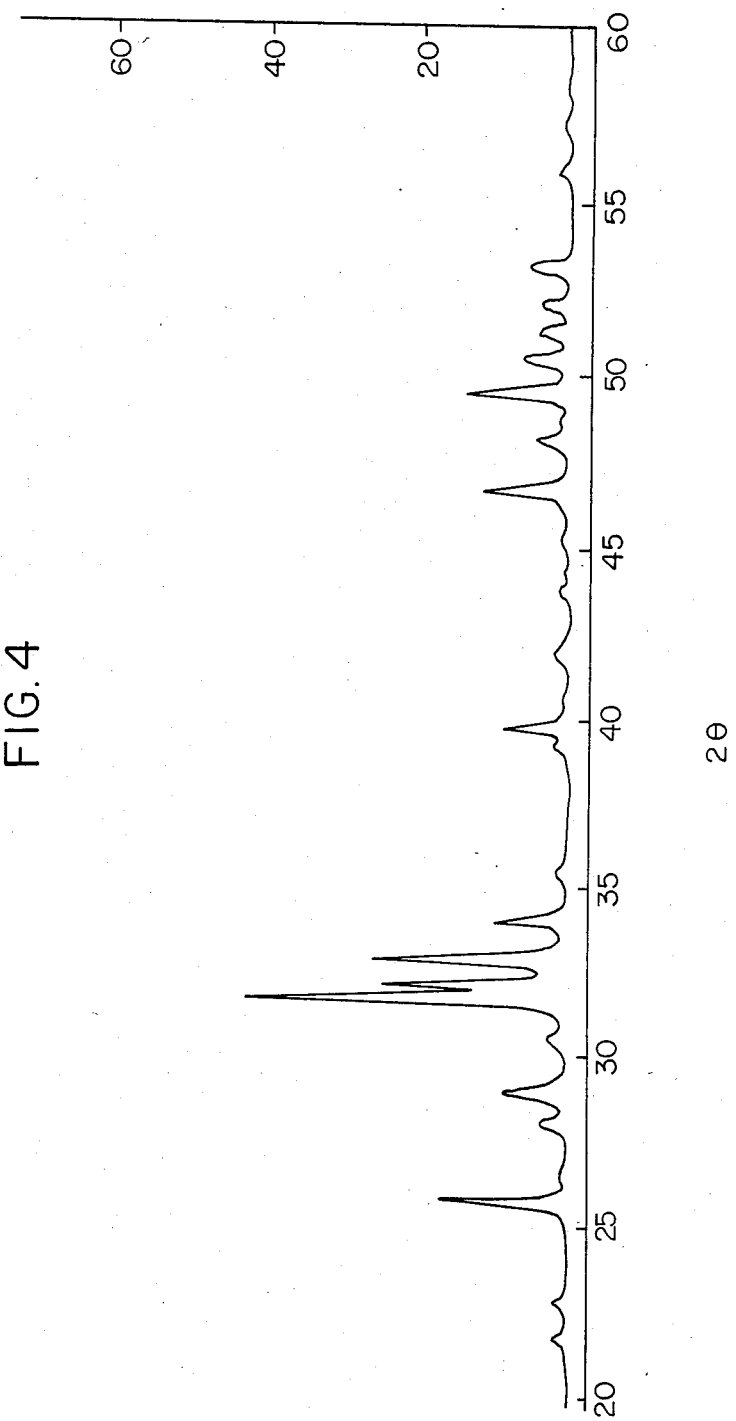
FIG. 4 is an X-ray diffraction pattern of the cotton-like product of hydroxy-apatite shown in FIG. 3 prior to being calcined.

11 weight % of pullulan particles having a mean molecular weight of 200,000, 17 weight % of hydroxy-apatite particles having a particle diameter of 50 to 800 Å, and 72 weight % of water were kneaded together to disperse the hydroxy-apatite uniformly in the aqueous pullulan solution. The thus prepared solution was defoamed and fed into a spinning apparatus as shown in FIG. 1 at a room temperature (25° C.), said apparatus equipped with a die having a plurality of 0.3 mm diameter spinning nozzles arrayed in a straight line in a transverse direction. The solution was extruded through the nozzles at a pressure of 1.4 kg/cm² while discharging air through the air gaps at a velocity of 250 m/sec to thereby form a stream of fibers. This fiber stream was heated on its opposite sides at a temperature of 400° C. by a far infrared heater (wavelength: 2 to 50 μm) underlying the spinning nozzles to evaporate the water off and was blown onto a screen type belt to produce a fibrous product in cotton-like form of hydroxy-apatite bonded by pullulan. The thus produced cotton-like product was heated at a heating rate of 50° C./hr. to be calcined at 1100° C. for an hour, whereby a cotton-like product of hydroxy-apatite having a mean fiber diameter of 5 μm and a mean fiber length of 50 mm was obtained as the pullulan was burned off. It was determined by X-ray diffraction and infrared ray spectrophotometry that the thus obtained cotton-like product contained substantially the same amount of hydroxy group as the starting material had. FIGS. 3 and 4 show X-ray diffraction patterns prior to and after the calcining step, respectively.

EXAMPLE 2

Pullulan particles with a mean molecular weight of 200,000 were dissolved in water to prepare 21 weight % of aqueous solution into which 6 weight % of hydroxy-apatite particles having a particle diameter of 50 to 300 Å was mixed. The solution was then defoamed. The thus prepared feed solution was fed into the apparatus used in the Example 1 at a room temperature and extruded at a pressure of 1.4 kg/cm$^2$ while discharging air through the air gaps at a velocity of 500 m/sec. to thereby form a stream of fibers. This fiber stream was heated on its opposite sides at a temperature of 400° C. by a far infrared heater (wavelength: 2-50 μm) underlying the spinning nozzles to evaporate the water off and was blown onto a screen type belt to produce a fibrous product in cotton-like form of hydroxy-apatite bonded by pullulan. The thus produced cotton-like product was heated at a heating rate of 50° C./hr. to be calcined at 1400° C. for two hours, whereby a cotton-like product of apatite having a mean fiber diameter 3 μm and a mean fiber length of 30 mm was obtained as the pullulan was burned off. It was determined by X-ray diffraction and infrared ray spectrophotometry that the thus obtained cotton-like product had been deprived of the hydroxy group.

EXAMPLE 3

A cotton-like product of hydroxy-apatite having a mean fiber diameter of 15 μm and a mean fiber length of 70 mm after calcined was obtained by the same procedure as the Example 1 except that the amounts of the pullulan particles, hydroxy-apatite particles, and water used were 19%, 31%, and 50% by weight, respectively.

EXAMPLE 4

A cotton-like product of hydroxy-apatite having a mean fiber diameter of 7 μm and a mean fiber length of 65 mm after calcined was obtained by the same procedure as the Example 1 except that polyvinyl alcohol with a molecular weight of 190,000 was used as a binder.

EXAMPLE 5

A cotton-like product of hydroxy-apatite having a mean fiber diameter of 3 μm and a mean fiber length of 35 mm was obtained by forming a stream of fibers under the same conditions as in the Example 1 except that a feed solution containing 50 weight % of hydroxy-apatite particles and 15 weight % of pullulan particles was used and that the air was discharged at a velocity of 1200 m/sec.

EXAMPLE 6

11 weight % of pullulan particles having a mean molecular weight of 200,000, 17 weight % of hydroxy-apatite particles having a particle diameter of 50 to 800 Å, and 72 weight % of water were kneaded together to disperse the hydroxy-apatite uniformly in the aqueous pullulan solution. The thus prepared solution was defoamed and fed into a spinning apparatus as shown in FIG. 2 at a room temperature (25° C.). The solution was extruded through the nozzles at a pressure of 1.4 kg/cm$^2$ while discharging air through the air gaps at a velocity of 250 m/sec to thereby form a stream of fibers. This fiber stream was heated on its opposite sides at a temperature of 400° C. by a far infrared heater (wavelength: 2 to 50 μm) underlying the spinning nozzles to evaporate the water off and was blown onto a screen type belt to produce a fibrous product in nonwoven fabric form of hydroxy-apatite bonded by pullulan. The thus produced nonwoven fabric was heated at a heating rate of 50° C./hr. to be calcined at 1100° C. for an hour, whereby a nonwoven fabric of hydroxy-apatite having a mean fiber diameter of 5 μm and a basis weight of 200 g/m$^2$ was obtained as the pullulan was burned off. It was determined by X-ray diffraction and infrared ray spectrophotometry that the thus obtained nonwoven fabric contained substantially the same amount of hydroxy group as the starting material had. FIG. 5 shows the fibers of the nonwoven fabric prior to and after the calcining step observed by electron micrographs.

EXAMPLE 7

Pullulan particles with a mean molecular weight of 200,000 were dissolved in water to prepare 21 weight % of aqueous solution into which 6 weight % of hydroxy-apatite particles having a particle diameter of 50 to 300 Å was mixed. The solution was then defoamed. The thus prepared feed solution was fed into the apparatus used in the Example 6 at a room temperature and extruded at a pressure of 1.4 kg/cm$^2$ while discharging air through the air gaps at a velocity of 500 m/sec. to thereby form a stream of fibers. This fiber stream was heated on its opposite sides at a temperature of 400° C. by a far infrared heater (wavelength: 2–50 μm) underlying the spinning nozzles to evaporate the water off and was blown onto a screen type belt to produce a fibrous product in nonwoven fabric form of hydroxy-apatite bonded by pullulan. The thus produced nonwoven fabric was heated at a heating rate of 50° C./hr. to be calcined at 1400° C. for two hours, whereby a nonwoven fabric of apatite having a mean fiber diameter 3 μm a basis weight of 200 g/m$^2$ was obtained as the pullulan was burned off. It was determined by X-ray diffraction and infrared ray spectrophotometry that the thus obtained nonwoven fabric had been deprived of the hydroxy group.

EXAMPLE 8

A nonwoven fabric of hydroxy-apatite having a mean fiber diamter of 15 μm after calcined was obtained by the same procedure as the Example 6 except that the amounts of the pulluran particles, hydroxy-apatite particles, and water used were 19%, 31%, and 50% by weight, respectively.

EXAMPLE 9

A nonwoven fabric of hydroxy-apatite having a mean diameter of 7 μm after calcined was obtained by the same procedure as the Example 6 except that polyvinyl alcohol with a molecular weight of 190,000 was used as a binder.

EXAMPLE 10

This example was conducted according to the Example 6 except that the composition of the viscous dispersion in the feedstock tank 2 comprised 25% of water, 35% of hydroxy-apatite, 30% of calcium phosphate and 10% of pullulan on the basis of weight. The spinning nozzles were 0.3 mm in diameter, the spinning temperature was a room temperature (25° C.), and the pressure of the air discharged was 300–1000 mm H$_2$O.

Further, the far infrared heater 9 was 800 to 1000 mm in length, had an output of 4 to 10 kw and provided heating temperature of 400° C. The nonwoven fabric of apatite was heated at a heating rate of 50° C./hr. to be calcined at 1100° C. for two hours.

The calcined apatite fibers produced in the examples described above had a mean fiber diameter of 3–15 μm and high mechanical strength, that is, high tensile strength and impact resistance.

ADVANTAGES OF THE INVENTION

From the foregoing, it is to be appreciated that since the apatite is solution spun at a room temperature rather than being melted at a high temperature, the present invention provides a fibrous product of apatite in cotton-like form and nonwoven fabric form which is not deprived of the hydroxy group loss of which would spoil the affinity with living organism in contrast to the prior art. Consequently, there is no need for after-treatments for imparting 'affinity' to the fabric product of apatite, lending itself to simplification of the manufacturing process and improved operating efficiency. It is believed that the solution spinning at a room temperature has been made possible by the fact that binders such as pulluran has been found out which meet the three conditions of non-toxicity to living organism, water-solubility and decomposability at a high temperature without melting, and that a conventional spinning apparatus used for the so-called melt blow process or melt spinning process has been so modified that a fibrous product of apatite may be produced by spinning feed solution through the spinning nozzles to form a stream of fibers without melting the material at a high temperature, heating the stream of fibers to evaporate the water off the fibers, and blowing the fiber stream onto a collector such as a collector plate or a screen type drum collector conventionally used for the melt blow process.

The present invention is the first that has succeeded in obtaining a high strength fibrous apatite by the solution spinning process by which it has heretofore been considered impossible to produce such apatite. A fibrous product, particularly cotton-like product or nonwoven fabric of apatite produced according to this invention is not deprived of the hydroxy group, exhibiting much the same affinity with living organism as the conventional sintered apatite. Furthermore, the content of hydroxy-apatite in the fibrous apatite may be adjusted by varying the calcining temperature to control the physical properties such as strength. In addition, owing to its fibrous form, the apatite material according to this invention provides high resistance to impact and superior processing characteristics, so that it may be easily conformed to intricate contours of breaks in a bone. Thus, the fibrous apatite of this invention may be used not only for artificial teeth but also for reconstruction of various bones and artificial joints. Further, it may be used for three-dimensional culture media in biotechnology.

While various embodiments of the invention have been described hereinabove, the present invention should not be limited to these, but various changes and modifications may be made without departing from the spirit and scope of the invention.

We claim:

1. An apatite fiber comprising one or more apatites selected from a group of apatites represented by the general formula:

$$M_{10}(ZO_4)_6X_2$$

wherein M represents Ca, Ba, Mg, Sr, Pb, Cd, Fe and the like $ZO_4$ represents $PO_4$, $AsO_4$, $VO_4$, $CO_3$ and the like, and X represents F, Cl, OH and the like.

2. The apatite fiber according to claim 1 wherein M is at least one selected from Ca, Ba, and Sr, $ZO_4$ is at least one selected from $PO_4$, $VO_4$ and $CO_3$, and X is at least one selected from OH and F.

3. The apatite fiber according to claim 1, substantially all of said apatite being hydroxy-apatite wherein M is Ca, $ZO_4$ is $PO_4$, and X is OH.

4. The apatite fiber according to claim 3 said apatite containing calcium phosphate type compound in addition to said hydroxy-apatite.

5. The apatite fiber according to claim 4 comprising 5 to 95 weight % of hydroxy-apatite and 95 to 5 weight % of calcium phosphate type compound.

6. The apatite fiber according to claim 5 wherein said hydroxy-apatite is 20 weight % or more and said calcium phosphate type compound is 80 weight % or less.

7. The apatite according to claim 5 wherein said hydroxy-apatite is 50 weight % or more and said calcium phosphate type compound is 50 weight % or less.

8. The apatite fiber according to any of claims 4 to 7 wherein said calcium phosphate type compound is at least one selected from a group of calcium hydrogen phosphate, tri-calcium phosphate and tetra-calcium phosphate.

9. The apatite fiber according to any of claims 1 to 8 which has a mean fiber diameter of 1 $\mu m$ to 30 $\mu m$ and a mean fiber length of 1 mm to 1000 mm.

10. The apatite fiber according to any of claims 1 to 9 which is made in the form of cotton-like product or nonwoven fabric.

11. The apatite fiber according to claim 10 wherein the basis weight of said nonwoven fabric is in the range of 5 $g/m^2$ to 200 $g/m^2$.

12. A method of producing a fibrous apatite in cotton-like form comprising the steps of:
(a) preparing a dispersion of apatite by dispersing fine apatite particles uniformly in a solution of binder in water, said apatite being one or more apatites selected from a group of apatites represented by the general formula:

$$M_{10}(ZO_4)_6X_2$$

wherein M represents Ca, Ba, Mg, Sr, Pb, Cd, Fe and the like, $ZO_4$ represents $PO_4$, $AsO_4$, $VO_4$, $CO_3$ and the like, and X represents F, Cl, OH and the like;
(b) continuously extruding the thus prepared dispersion through a plurality of spinning orifices while simultaneously stretching the dispersion into a fibrous state with the aid of a high speed air flow to form a stream of fine fibers;
(c) heating said fiber stream to evaporate the water in the fibers;
(d) blowing said water-removed fiber stream upon a collector means to form a cotton-like product of apatite bonded by the binder; and
(e) if required, calcining said cotton-like product.

13. The method according to claim 12 further including the step of making the cotton-like product of apatite in the form of nonwoven fabric.

14. The method according to claims 12 or 13 wherein said apatite used is an apatite in which M is Ca, $ZO_4$ is $PO_4$ and X is OH.

15. The method according to claims 12 or 13 wherein said apatite used is a hydroxy-apatite in which M is Ca, $ZO_4$ is $PO_4$ and X is OH.

16. The method according to claims 12 or 13 wherein said apatite particles are in the form of stick having a mean particle diameter of 50 Å to 1 μm.

17. The method according to claims 12 or 13 wherein said binder is a water-soluble high molecular compound.

18. The method according to claim 17 wherein said binder is pullulan.

19. The method according to claims 12 or 13 wherein said apatite dispersion further contains fine particles of calcium phosphate type compound.

20. The method according to claims 12 or 13 wherein said fiber stream is heated so that the moisture content of the fibers is reduced to 10% or less.

21. The method according to claims 12 or 13 wherein said calcining temperature is in the range of 500° C. to 1250° C.

22. The method according to claim 21 wherein said calcining temperature is in the range of 650° C. to 1100° C.

23. A cotton-like product formed by intertwined apatite fiber of claim 1.

24. Non-woven fabric of the apatite fiber of claim 1.

* * * * *